United States Patent
Edwards et al.

(10) Patent No.: US 9,738,641 B2
(45) Date of Patent: Aug. 22, 2017

(54) BICYCLIC INHIBITORS

(71) Applicant: Kalvista Pharmaceuticals Limited, Salisbury (GB)

(72) Inventors: Hannah Joy Edwards, Salisbury (GB); David Michael Evans, Salisbury (GB); Rebecca Louise Davie, Salisbury (GB); David Philip Rooker, Salisbury (GB); Steven John Hewison, Hinckley (GB)

(73) Assignee: Kalvista Pharmaceuticals Limited, Salisbury (GB)

( * ) Notice: Subject to any disclaimer, the term of this patent is extended or adjusted under 35 U.S.C. 154(b) by 0 days.

(21) Appl. No.: 14/907,095

(22) PCT Filed: Aug. 14, 2014

(86) PCT No.: PCT/GB2014/052511
§ 371 (c)(1),
(2) Date: Jan. 22, 2016

(87) PCT Pub. No.: WO2015/022547
PCT Pub. Date: Feb. 19, 2015

(65) Prior Publication Data
US 2016/0185773 A1 Jun. 30, 2016

Related U.S. Application Data

(60) Provisional application No. 61/865,696, filed on Aug. 14, 2014.

(30) Foreign Application Priority Data

Aug. 14, 2013 (GB) .................................... 1314578.4

(51) Int. Cl.
| | | |
|---|---|---|
| A61K 31/535 | (2006.01) | |
| A01N 43/42 | (2006.01) | |
| A61K 31/44 | (2006.01) | |
| C07D 265/36 | (2006.01) | |
| C07D 498/02 | (2006.01) | |
| C07D 471/02 | (2006.01) | |
| C07D 491/02 | (2006.01) | |
| C07D 513/02 | (2006.01) | |
| C07D 515/02 | (2006.01) | |
| C07D 471/04 | (2006.01) | |
| A61K 31/5365 | (2006.01) | |
| C07D 401/04 | (2006.01) | |
| C07D 413/04 | (2006.01) | |
| C07D 519/00 | (2006.01) | |

(52) U.S. Cl.
CPC ........ *C07D 471/04* (2013.01); *A61K 31/5365* (2013.01); *C07D 401/04* (2013.01); *C07D 413/04* (2013.01); *C07D 519/00* (2013.01)

(58) Field of Classification Search
None
See application file for complete search history.

(56) References Cited

U.S. PATENT DOCUMENTS

| 5,187,157 A | 2/1993 | Kettner et al. |
| 5,786,328 A | 7/1998 | Dennis et al. |
| 2015/0315198 A1 | 11/2015 | Li et al. |
| 2016/0039752 A1 | 2/2016 | Allan et al. |

FOREIGN PATENT DOCUMENTS

| EP | 2281885 | 2/2011 |
| WO | WO 92/04371 | 3/1992 |
| WO | WO 94/29335 | 12/1994 |
| WO | WO 95/07921 | 3/1995 |
| WO | WO 03/076458 | 9/2003 |
| WO | WO 2005/123680 | 12/2005 |
| WO | WO 2006/025714 A1 | 3/2006 |
| WO | WO 2007/001139 A1 | 1/2007 |
| WO | WO 2008/016883 | 2/2008 |
| WO | WO 2008/049595 | 5/2008 |
| WO | WO 2010/142801 | 12/2010 |
| WO | WO 2011/118672 | 9/2011 |
| WO | WO 2012/004678 | 1/2012 |
| WO | WO 2012/017020 | 2/2012 |
| WO | WO 2013/111107 | 8/2013 |
| WO | WO 2013/111108 | 8/2013 |
| WO | WO 2015/134998 A1 | 9/2015 |
| WO | WO 2015/171526 A2 | 11/2015 |
| WO | WO 2015/171527 A1 | 11/2015 |
| WO | WO 2016/011209 A1 | 1/2016 |

OTHER PUBLICATIONS

A Simple, Sensitive and Selective Fluorogenic Assay to Monitor Plasma Kallikrein Inhibitory Activity of BCX4161 in Activated Plasma, BioCryst Pharmaceuticals, Inc., Journal of Allergy and Clinical Immunology, Feb. 2014, 133(2 Supp),Abstract AB40, p. 1.

(Continued)

*Primary Examiner* — Jeffrey H Murray
(74) *Attorney, Agent, or Firm* — Baker & Hostetler LLP

(57) ABSTRACT

The present invention provides compounds of formula (I): compositions comprising such compounds; the use of such compounds in therapy (for example in the treatment or prevention of a disease or condition in which plasma kallikrein activity is implicated); and methods of treating patients with such compounds; wherein A, B, W, X and Y are as defined herein.

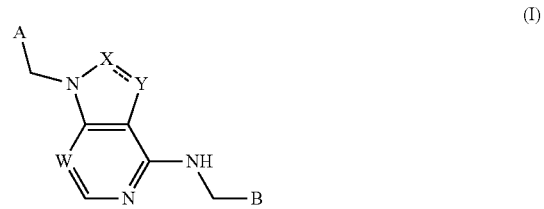

(I)

29 Claims, No Drawings

(56) References Cited

OTHER PUBLICATIONS

"BCX4161, an Oral Kallikrein Inhibitor: Safety and Pharmacokinetic Results of a Phase 1 Study in Healthy Volunteers", BioCryst Pharmaceuticals, Inc., Journal of Allergy and Clinical Immunology, Feb. 2014, 133(2 Supp),Abstract AB39, p. 1.
Bhoola et al., "Bioregulation of Kinins: Kallikreins, Kininogens and Kininases", Pharmacological Rev., Mar. 1992, 44(1), 1-80.
Bryant et al., "Human Plasma Kallikrein-Kinin System: Physiological and Biochemical Parameters", Cardiovascular & Hematological Agents in Medicinal Chemistry, Jul. 2009, 234-250.
Caddick et al., "Convenient Synthesis of Protected Primary Amines From Nitriles", Tetrahedron Letters, Apr. 2000, 41, 3513-3516.
Campbell, "Towards Understanding the Kallikrein-Kinin System: Insights from the Measurement of Kinin Peptides", Brazilian Journal of Medical and Biological Research, Jun. 2000, 33(6), 665-677.
Chilcote et al., "ASP-634: An Oral Drug Candidate for Diabetic Macular Edema", ARVO, Mar. 2012, Presentation 2240, Abstract, p. 1.
Clermont et al., "Plasma Kallikrein Mediates Retinal Vascular Dysfunction and Induces Retinal Thickening in Diabetic Rats", Diabetes, May 2011, 60(5), 1590-1598.
Elman et al., "Randomized Trial Evaluating Ranibizumab Plus Prompt or Deferred Laser or Triamcinolone Plus Prompt Laser for Diabetic Macular Edema", Ophthalmology, Jun. 2010, 117(6), e35, 1064-1077.
Evans et al., "Selective Inhibitors of Plasma Kallikrein", Immunopharmacology, May 1996, 32(1-3), 115-116.
Garrett et al. "Peptide Aldehyde Inhibitors of the Kallikreins: an Investigation of Subsite Interactions with Tripeptides Containing Structural Variations at the Amino Terminus", J. Peptide Research, Jul. 1998, 52(1), 60-71.
Griesbacher et al., Involvement of Tissue Kallikrein But Not Plasma Kallikrein in the Development of Symptoms Mediated by Endogenous Kinins in Acute Pancreatitis in Rats, British Journal of Pharmacology, Nov. 2002, 137, 692-700.
Johansen et al., "Assay of Kallikrein Inhibitors and Levels of Acetone-Activated Kallikrein in Plasma Specimens From Reactors to Dextran or to Contrast Media", Bioscience Ed, Int. J. Tiss. Reac., 1986, 185-192.
Kolte et al., "Biochemical Characterization of a Novel High-Affinity and Specific Kallikrein Inhibitor", British Journal of Pharmacology, Apr. 2011, 162, 1639-1649.
Lehmann, "Ecallantide (DX-88), A Plasma Kallikrein Inhibitor for the Treatment of Hereditary Angioedema and the Prevention of Blood Loss in On-Pump Cardiothoracic Surgery", Expert Opinion on Biological Therapy, Jul. 2008, 8(8), 1187-1199.
Leinweber et al, "Possible Physiological Roles of Carboxylic Ester Hydrolases", Drug Metabolism Reviews, Jan. 1987, 18(4), 379-439.
Liang et al., "Fast Dissolving Intraoral Drug Delivery Systems", Expert Opinion in Therapeutic Patents, Jun. 2001, 11(6), 981-986.
Lieberman et al., "Pharmaceutical Dosage Forms: Tablets", Marcel Dekker, Inc., 1980, 145-157.
Marceau et al., "Bradykinin Receptor Ligands: Therapeutic Perspectives", Nature Reviews Drug Discovery, Oct. 2004, 3, 845-852.
Okada et al.; "Development of Potent and Selective Plasmin and Plasma Kallikrein Inhibitors and Studies on the Structure-Activity Relationship", Chem. Pharm. Bull., Sep. 2000, 48(12), 1964-1972.
Patel, "Combination Therapy for Age-Related Macular Degeneration", Retina, Jun. 2009, 29(6), S45-S48.
Shori et al., "New Specific Assays for Tonin and Tissue Kallikrein Activities in Rat Submandibular Glands", Biochemical Pharmacology, Mar. 1992, 43(6), 1209-1217.
Stahl, "A Handbook of Pharmaceutical Salts: Properties, Selection and Use", Wiley-VCH, Weinheim, Germany, 2002, 24(3), p. 20.
Sturzbecher et al., "Inhibition of Human Mast Cell Tryptase by Benzamidine Derivatives", Biol. Chem. Hoppe-Seyler, Oct. 1992, 373, 1025-1030.
Sturzebecher et al., "Novel Plasma Kallikrein Inhibitors of the Benzamidine Type", Brazilian J. Med. Biol. Res., Aug. 1994, 27(8), 1929-1934.
Teno et al., "Development of Active Center-Directed Plasmin and Plasma Kallikrein Inhibitors and Studies on the Structure-Inhibitory Activity Relationship", Chemical and Pharmaceutical Bulletin, Jun. 1993, 41(6), 1079-1090.
Wermuth, "The Practice of Medicinal Chemistry", 2003, 2nd Ed., 561-585.
Young et al., "Small Molecule Inhibitors of Plasma Kallikrein", Bioorganic & Medicinal Chemistry Letters, Apr. 2006, 16(7), 2034-2036.
Zhang et al., "Discovery of Highly Potent Small Molecule Kallikrein Inhibitors"; Medicinal Chemistry, Nov. 2006, 2(6), 545-553.
Liu et al.; "Hyperglycemia Induced Cerebral Hematoma Expansion is Mediated by Plasma Kallikrein"; Nat. Med.; Feb. 2011; vol. 17(2); p. 206-210.
Bjorkqvist et al.; "Plasma kallikrein: the bradykinin-producing enzyme"; Thrombosis and Haemostasis; Jul. 11, 2013; vol. 110; p. 399-407.
Katsuura et al.; "Effects of a Highly Selective Synthetic Inhibitor of Plasma Kallikrein on Disseminated Intravascular Coagulation in Rats"; Thrombosis Research; May 15, 1996; vol. 82 No. 4; p. 361-368.
Bird et al.; Effects of plasma kallikrein deficiency on haemostasis and thrombosis in mice: Murine Ortholog of the Fletcher Trait Thrombosis and Haemostasis; Mar. 8, 2012; vol. 107; p. 1141-50.
Revenko et al.; "Selective depletion of plasma prekallikrein or coagulation factor XII inhibits thrombosis in mice without increased risk of bleeding"; Blood; Aug. 5, 2011; 118; p. 5302-5311.
Feener et al.; "Role of plasma kallikrein in diabetes and metabolism"; Thrombosis and Haemostasis; Sep. 2013; vol. 110(3); p. 434-441.
Tombran-Tink et. al; "Visual Dysfunction in Diabetes: The Science of Patient Impairment and Health Care"; Humana Press; 2012; p. 34.
Bryant et al.; "Human Plasma Kallikrein-Kinin System: Physiological and Biochemical Parameters"; Cardiovascular & Hematological Agents in Medicinal Chemistry; Jul. 2009; vol. 7; p. 234-250.
Jaffa et al.; "A Risk Marker for Hypertension and Nephropathy in Type 1 Diabetes"; Diabetes; May 2003; vol. 52; p. 1215-1221.
Davis III et al.; "Biological activities of C1 inhibitor"; Molecular Immunology; Oct. 2008; vol. 45; p. 4057-4063.
Colman et al.; "Plasma and tissue kallikrein in arthritis and inflammatory bowel disease" Immunopharmacology; Sep. 1999; vol. 43; p. 103-108.
Siebeck et al.; "Inhibition of Plasma Kallikrein With Aprotinin in Porcine Endotoxin Shock"; Journal of Trauma; Feb. 1993; vol. 34 No. 2; p. 193-198.
Ikeda et al.; "Host Stromal Bradykinin B2 Receptor Signaling Facilities Tumor-Associated Angiogenesis and Tumor Growth"; Cancer Research; Aug. 2004; vol. 64; p. 5178-5185.
Greisbacher et al.; "Involvement of tissue kallikrein but not plasma kallikrein in the development of symptoms mediated by endogenous kinins in acute pancreatitis in rats"; British Journal of Pharmacology; Nov. 2002; vol. 137(5); p. 692-700.
Bhoola et al.; "Kallikrein-Kinin Cascade"; Encyclopedia of Respiratory Medicine; 2006; 11 pages.
Collis et al.; "BCX4161, An Oral Kallikrein Inhibitor: Safety and Pharmacokinetic Results of a Phase 1 Study in Healthy Volunteers"; Journal of Allergy and Clinical Immunology; Feb. 2014; vol. 133 Issue 2; p. AB39.
Babu et al.; "A Simple, Sensitive and Selective Fluorogenic Assay to Monitor Plasma Kallikrein Inhibitory Activity of BCX4161 in Activated Plasma"; Journal of Allergy and Clinical Immunology; Feb. 2014; vol. 133 Issue 2; p. AB40.
Remington: Practice of the Science and Pharmacy; $19^{th}$ Edition; Mack Publishing; 1995; 5 pages.

BICYCLIC INHIBITORS

CROSS-REFERENCE TO RELATED APPLICATIONS

This application is the National Stage of International Patent Application No. PCT/GB2014/052511 filed Aug. 14, 2014, which claims the benefit of Great Britain Patent Application No. 1314578.4, filed Aug. 14, 2013 and U.S. Provisional Patent Application No. 61/865,696, filed Aug. 14, 2013, the disclosures of which are incorporated herein by reference in their entireties.

This invention relates to bicyclic derivatives that are inhibitors of plasma kallikrein and to pharmaceutical compositions containing and the uses of, such derivatives.

BACKGROUND TO THE INVENTION

The bicyclic derivatives of the present invention are inhibitors of plasma kallikrein and have a number of therapeutic applications, particularly in the treatment of retinal vascular permeability associated with diabetic retinopathy and diabetic macular edema.

Plasma kallikrein is a trypsin-like serine protease that can liberate kinins from kininogens (see K. D. Bhoola et al., "Kallikrein-Kinin Cascade", *Encyclopedia of Respiratory Medicine*, p 483-493; J. W. Bryant et al., "Human plasma kallikrein-kinin system: physiological and biochemical parameters" *Cardiovascular and haematological agents in medicinal chemistry*, 7, p 234-250, 2009; K. D. Bhoola et al., *Pharmacological Rev.*, 1992, 44, 1; and D. J. Campbell, "Towards understanding the kallikrein-kinin system: insights from the measurement of kinin peptides", *Brazilian Journal of Medical and Biological Research* 2000, 33, 665-677). It is an essential member of the intrinsic blood coagulation cascade although its role in this cascade does not involve the release of bradykinin or enzymatic cleavage. Plasma prekallikrein is encoded by a single gene and synthesized in the liver. It is secreted by hepatocytes as an inactive plasma prekallikrein that circulates in plasma as a heterodimer complex bound to high molecular weight kininogen which is activated to give the active plasma kallikrein. Kinins are potent mediators of inflammation that act through G protein-coupled receptors and antagonists of kinins (such as bradykinin antagonists) have previously been investigated as potential therapeutic agents for the treatment of a number of disorders (F. Marceau and D. Regoli, Nature Rev., Drug Discovery, 2004, 3, 845-852).

Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastro-intestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (A. Lehmann "Ecallantide (DX-88), a plasma kallikrein inhibitor for the treatment of hereditary angioedema and the prevention of blood loss in on-pump cardiothoracic surgery" *Expert Opin. Biol. Ther.* 8, p 1187-99).

The plasma kallikrein-kinin system is abnormally abundant in patients with advanced diabetic macular edema. It has been recently published that plasma kallikrein contributes to retinal vascular dysfunctions in diabetic rats (A. Clermont et al. "Plasma kallikrein mediates retinal vascular dysfunction and induces retinal thickening in diabetic rats" *Diabetes*, 2011, 60, p 1590-98). Furthermore, administration of the plasma kallikrein inhibitor ASP-440 ameliorated both retinal vascular permeability and retinal blood flow abnormalities in diabetic rats. Therefore a plasma kallikrein inhibitor should have utility as a treatment to reduce retinal vascular permeability associated with diabetic retinopathy and diabetic macular edema.

Other complications of diabetes such as cerebral haemorrhage, nephropathy, cardiomyopathy and neuropathy, all of which have associations with plasma kallikrein may also be considered as targets for a plasma kallikrein inhibitor.

Synthetic and small molecule plasma kallikrein inhibitors have been described previously, for example by Garrett et al. ("Peptide aldehyde . . . " *J. Peptide Res.* 52, p 62-71 (1998)), T. Griesbacher et al. ("Involvement of tissue kallikrein but not plasma kallikrein in the development of symptoms mediated by endogenous kinins in acute pancreatitis in rats" *British Journal of Pharmacology* 137, p 692-700 (2002)), Evans ("Selective dipeptide inhibitors of kallikrein" WO03/076458), Szelke et al. ("Kininogenase inhibitors" WO92/04371), D. M. Evans et al. (*Immunolpharmacology*, 32, p 115-116 (1996)), Szelke et al. ("Kininogen inhibitors" WO95/07921), Antonsson et al. ("New peptides derivatives" WO94/29335), J. Corte et al. ("Six membered heterocycles useful as serine protease inhibitors" WO2005/123680), J. Stürzbecher et al. (*Brazilian J. Med. Biol. Res* 27, p 1929-34 (1994)), Kettner et al. (U.S. Pat. No. 5,187,157), N. Teno et al. (*Chem. Pharm. Bull.* 41, p 1079-1090 (1993)), W. B. Young et al. ("Small molecule inhibitors of plasma kallikrein" *Bioorg. Med. Chem. Letts.* 16, p 2034-2036 (2006)), Okada et al. ("Development of potent and selective plasmin and plasma kallikrein inhibitors and studies on the structure-activity relationship" *Chem. Pharm. Bull.* 48, p 1964-72 (2000)), Steinmetzer et al. ("Trypsin-like serine protease inhibitors and their preparation and use" WO08/049595), Zhang et al. ("Discovery of highly potent small molecule kallikrein inhibitors" *Medicinal Chemistry* 2, p 545-553 (2006)), Sinha et al. ("Inhibitors of plasma kallikrein" WO08/016883), Shigenaga et al. ("Plasma Kallikrein Inhibitors" WO2011/118672), and Kolte et al. ("Biochemical characterization of a novel high-affinity and specific kallikrein inhibitor", British Journal of Pharmacology (2011), 162(7), 1639-1649). Also, Steinmetzer et al. ("Serine protease inhibitors" WO2012/004678) describes cyclized peptide analogs which are inhibitors of human plasmin and plasma kallikrein.

To date, no small molecule synthetic plasma kallikrein inhibitor has been approved for medical use. The molecules described in the known art suffer from limitations such as poor selectivity over related enzymes such as KLK1, thrombin and other serine proteases, and poor oral availability. The large protein plasma kallikrein inhibitors present risks of anaphylactic reactions, as has been reported for Ecallantide. Thus there remains a need for compounds that selectively inhibit plasma kallikrein, that do not induce anaphylaxis and that are orally available. Furthermore, the vast majority of molecules in the known art feature a highly polar and ionisable guanidine or amidine functionality. It is well known that such functionalities may be limiting to gut permeability and therefore to oral availability. For example, it has been reported by Tamie J. Chilcote and Sukanto Sinha ("ASP-634: An Oral Drug Candidate for Diabetic MacularEdema", ARVO 2012 May 6-May 9, 2012, Fort Lauderdale, Fla., Presentation 2240) that ASP-440, a benzamidine, suffers from poor oral availability. It is further reported that absorption may be improved by creating a prodrug such as ASP-634. However, it is well known that prodrugs can suffer from several drawbacks, for example, poor chemical stability and potential toxicity from the inert carrier or from unexpected metabolites. In another report, indole amides are claimed as compounds that might overcome problems associated with drugs possessing poor or inadequate ADME-tox and physicochemical properties although no inhibition against plasma kallikrein is presented or claimed (Griffioen et al, "Indole amide derivatives and related compounds for use in the treatment of neurodegenerative diseases", WO2010, 142801).

BioCryst Pharmaceuticals Inc. have reported the discovery of the orally available plasma kallikrein inhibitor BCX4161 ("BCX4161, An Oral Kallikrein Inhibitor: Safety and Pharmacokinetic Results Of a Phase 1 Study In Healthy Volunteers", Journal of Allergy and Clinical Immunology, Volume 133, Issue 2, Supplement, February 2014, page AB39 and "A Simple, Sensitive and Selective Fluorogenic Assay to Monitor Plasma Kallikrein Inhibitory Activity of BCX4161 in Activated Plasma", Journal of Allergy and Clinical Immunology, Volume 133, Issue 2, Supplement February 2014, page AB40). However, human doses are relatively large, currently being tested in proof of concept studies at doses of 400 mg three times daily.

There are only few reports of plasma kallikrein inhibitors that do not feature guanidine or amidine functionalities. One example is Brandi et al. ("N-((6-amino-pyridin-3-yl) methyl)-heteroaryl-carboxamides as inhibitors of plasma kallikrein" WO2012/017020), which describes compounds that feature an aminopyridine functionality. Oral efficacy in a rat model is demonstrated at relatively high doses of 30 mg/kg and 100 mg/kg but the pharmacokinetic profile is not reported. Thus it is not yet known whether such compounds will provide sufficient oral availability or efficacy for progression to the clinic. Other examples are Brandi et al. ("Aminopyridine derivatives as plasma kallikrein inhibitors" WO2013/111107) and Flohr et al. ("5-membered heteroarylcarboxamide derivatives as plasma kallikrein inhibitors" WO2013/111108). However, neither of these documents report any in vivo data and therefore it is not yet known whether such compounds will provide sufficient oral availability or efficacy for progression to the clinic.

Therefore there remains a need to develop new plasma kallikrein inhibitors that will have utility to treat a wide range of disorders, in particular to reduce retinal vascular permeability associated with diabetic retinopathy and diabetic macular edema. Preferred compounds will possess a good pharmacokinetic profile and in particular will be suitable as drugs for oral delivery.

SUMMARY OF THE INVENTION

The present invention relates to a series of bicyclic derivatives that are inhibitors of plasma kallikrein. These compounds are potentially useful in the treatment of impaired visual acuity, diabetic retinopathy, macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery. The invention further relates to pharmaceutical compositions of the inhibitors, to the use of the compositions as therapeutic agents, and to methods of treatment using these compositions.

A compound of formula (I),

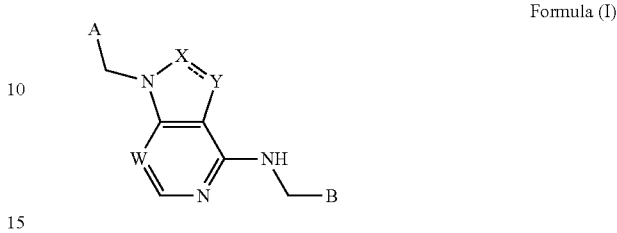

Formula (I)

wherein
W is selected from CH and N;
X is selected from CH, $CH_2$—$CH_2$, CH=CH, N and NH;
Y is selected from $CH_2$, CH, N, NH and O;
wherein the bond between X and Y ("===") is either saturated, unsaturated or aromatic;
B is selected from
i) a radical of formula II

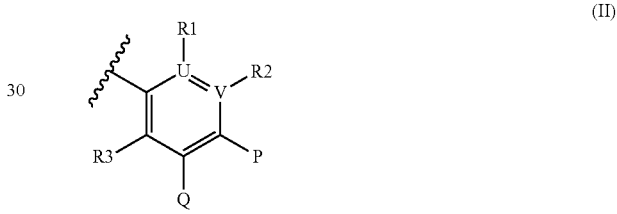

(II)

and
ii) a fused 6,5- or 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9;
P is H and Q is —C(R20)(R21)$NH_2$, or P is C(R20)(R21) $NH_2$ and Q is H;
U and V are independently selected from C and N such that the aromatic ring containing U and V is phenyl, pyridine or pyrazine;
R1 is absent when U is N;
R2 is absent when V is N;
or, when present, R1 and R2 are independently selected from H, alkyl, alkoxy, CN, halo and $CF_3$;
R3 is selected from H, alkyl, alkoxy, CN, halo and $CF_3$;
A is selected from —$(CH_2)_{0-9}$-heteroaryl and —$(CH_2)_{0-9}$-aryl;
R8 and R9 are independently selected from H and alkyl;
R20 and R21 are independently selected from H and alkyl, or may together form a cycloalkyl ring or a cyclic ether;
alkyl is a linear saturated hydrocarbon having up to 10 carbon atoms ($C_1$-$C_{10}$) or a branched saturated hydrocarbon of between 3 and 10 carbon atoms ($C_3$-$C_{10}$); alkyl may optionally be substituted with 1 or 2 substituents independently selected from ($C_1$-$C_6$)alkoxy, OH, CN, $CF_3$, COOR10, CONR10R11, fluoro and NR10R11;
cycloalkyl is a monocyclic saturated hydrocarbon of between 3 and 7 carbon atoms;

a cyclic ether is a monocyclic saturated hydrocarbon of between 4 and 7 carbon atoms, wherein one of the ring carbons is replaced by an oxygen atom;

alkoxy is a linear O-linked hydrocarbon of between 1 and 6 carbon atoms ($C_1$-$C_6$) or a branched O-linked hydrocarbon of between 3 and 6 carbon atoms ($C_3$-$C_6$); alkoxy may optionally be substituted with 1 or 2 substituents independently selected from OH, CN, $CF_3$, COOR10, CONR10R11, fluoro and NR10R11;

aryl is phenyl, biphenyl or naphthyl; aryl may be optionally substituted with 1, 2 or 3 substituents independently selected from alkyl, alkoxy, methylenedioxy, ethylenedioxy, OH, halo, CN, morpholinyl, piperidinyl, heteroaryl, —$(CH_2)_{0-3}$—O-heteroaryl, aryl$^b$, —O-aryl$^b$, —$(CH_2)_{1-3}$-aryl$^b$, —$(CH_2)_{1-3}$-heteroaryl, —COOR10, —CONR10R11, —$(CH_2)_{1-3}$—NR14R15, $CF_3$ and —NR10R11;

aryl$^b$ is phenyl, biphenyl or naphthyl, which may be optionally substituted with 1, 2 or 3 substituents independently selected from alkyl, alkoxy, OH, halo, CN, morpholinyl, piperidinyl, —COOR10, —CONR10R11, $CF_3$ and NR10R11;

heteroaryl is a 5, 6, 9 or 10 membered mono- or bi-cyclic aromatic ring, containing, where possible, 1, 2 or 3 ring members independently selected from N, NR8, S and O; heteroaryl may be optionally substituted with 1, 2 or 3 substituents independently selected from alkyl, alkoxy, OH, halo, CN, aryl, morpholinyl, piperidinyl, —$(CH_2)_{1-3}$-aryl, heteroaryl$^b$, —COOR10, —CONR10R11, $CF_3$ and —NR10R11;

heteroaryl$^b$ is a 5, 6, 9 or 10 membered mono- or bi-cyclic aromatic ring, containing, where possible, 1, 2 or 3 ring members independently selected from N, NR8, S and O; wherein heteroaryl$^b$ may be optionally substituted with 1, 2 or 3 substituents independently selected from alkyl, alkoxy, OH, halo, CN, morpholinyl, piperidinyl, aryl, —$(CH_2)_{1-3}$-aryl, —COOR10, —CONR10R11, $CF_3$ and NR10R11;

R10 and R11 are independently selected from H and alkyl; or R10 and R11 together with the nitrogen to which they are attached form a 4-, 5-, 6- or 7-membered heterocyclic ring which may be saturated or unsaturated with 1 or 2 double bonds;

R14 and R15 are independently selected from alkyl, aryl$^b$ and heteroaryl$^b$; or R14 and R15 together with the nitrogen to which they are attached form a 4-, 5-, 6- or 7-membered heterocyclic ring which may be saturated or unsaturated with 1 or 2 double bonds, and optionally may be oxo substituted;

and tautomers, isomers, stereoisomers (including enantiomers, diastereoisomers and racemic and scalemic mixtures thereof), pharmaceutically acceptable salts and solvates thereof.

In another aspect the present invention provides a prodrug of a compound of formula (I) as herein defined, or a pharmaceutically acceptable salt thereof.

In yet another aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

In an aspect, the invention comprises a subset of the compounds of formula I,

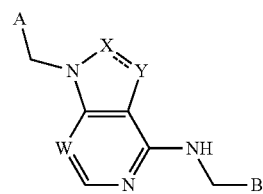

Formula (I)

wherein
W is selected from CH and N;
X is selected from CH, $CH_2$—$CH_2$, and N;
Y is selected from CH, N and O;
wherein the bond between X and Y ("═") is either saturated, unsaturated or aromatic;
wherein A and B are as previously defined above;
and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula I,

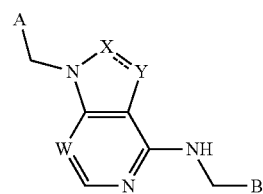

Formula (I)

wherein
W is selected from CH and N;
X is selected from CH and $CH_2$—$CH_2$;
Y is selected from CH and O;
wherein the bond between X and Y ("═") is either saturated, unsaturated or aromatic; wherein A and B are as previously defined above;
and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula I, as defined by formula (III),

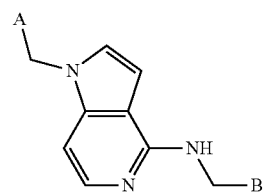

Formula (III)

wherein A and B are as previously defined above;
and tautomers, isomers, stereoisomers (including enantiomers, diastereoisomers and racemic and scalemic mixtures thereof), pharmaceutically acceptable salts and solvates thereof.

In an aspect, the invention comprises a subset of the compounds of formula I, as defined by formula (IV),

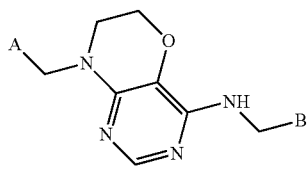

Formula (IV)

wherein A and B are as previously defined above;
and tautomers, isomers, stereoisomers (including enantiomers, diastereoisomers and racemic and scalemic mixtures thereof), pharmaceutically acceptable salts and solvates thereof.

The present invention also comprises the following aspects and combinations thereof:

Compounds of formula (I), formula (III) or formula (IV) wherein, A is selected from —$(CH_2)_{0-9}$-heteroaryl and —$(CH_2)_{0-9}$-aryl, wherein heteroaryl and aryl are as defined according to formula (I) above.

Compounds of formula (I), formula (III) or formula (IV) wherein, A is selected from heteroaryl substituted by phenyl; and $(CH_2)_{0-3}$phenyl substituted by heteroaryl, —$(CH_2)_{1-3}$-heteroaryl and —$(CH_2)_{1-3}$—NR14R15; wherein heteroaryl, R14 and R15 are as defined according to formula (I) above.

Preferred are compounds of formula (I), formula (III) or formula (IV) wherein, A is selected from $(CH_2)_{0-3}$phenyl,

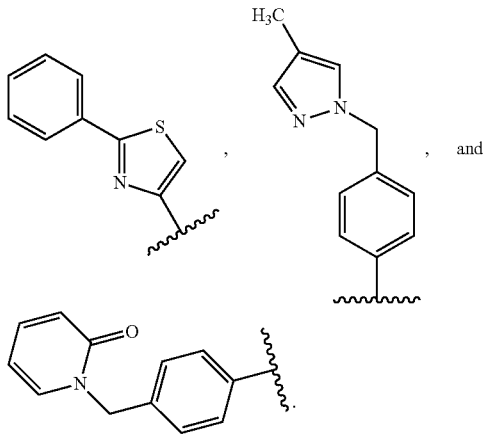

Most preferred are compounds of formula (I), formula (III) or formula (IV) wherein, A is selected from:

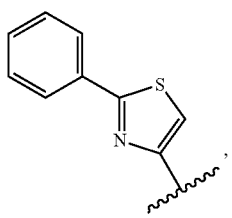 [SMILES: *c1csc(-c2ccccc2)n1]

phenyl, and

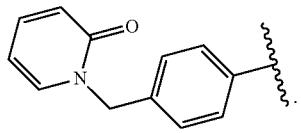 [SMILES: *c1ccc(Cn2ccccc2=O)cc1]

Compounds of formula (I), formula (III) or formula (IV) wherein, B is selected from:

i) a radical of formula II

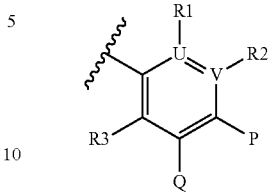

and ii) a fused 6,5- or 6,6-heteroaromatic bicyclic ring, containing N and, optionally, one or two additional heteroatoms independently selected from N, O and S, which is optionally mono-, di or tri-substituted with a substituent selected from alkyl, alkoxy, OH, halo, CN, COOR8, CONR8R9, $CF_3$ and NR8R9;

wherein R1, R2, R3, R8, R9, P, Q U, V, alkyl and alkoxy are as defined according to formula (I) above.

Compounds of formula (I), formula (III) or formula (IV) wherein, B is selected from:

i) a radical of formula IIa

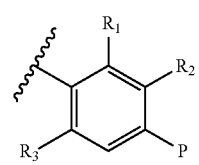

wherein R1 is selected from H and alkyl, R2 is H, R3 is selected from H and alkyl, and P is $CH_2NH_2$; and ii) a fused 6,5- or 6,6-heteroaromatic bicyclic ring, containing N and, optionally, one or two additional heteroatoms independently selected from N and O, which is optionally mono or di-substituted with a substituent selected from alkyl, alkoxy, OH, halo, CN, $CF_3$ and NR8R9;

wherein alkyl, alkoxy, R8 and R9 are as defined according to formula (I) above.

Compounds of formula (I) or formula (III) wherein, B is a radical of formula IIa,

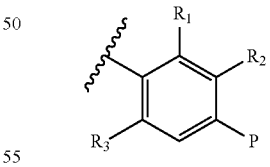

wherein R1 is selected from H and alkyl, R2 is H, R3 is selected from H and alkyl, and P is —$CH_2NH_2$; wherein alkyl is as defined according to formula (I) above.

Compounds of formula (I), formula (III) or formula (IV) wherein, B is selected from optionally substituted isoquinolinyl, wherein said optional substituent is selected from alkyl, alkoxy, OH, and NR8R9; and optionally substituted 1H-pyrrolo[2,3-b]pyridine, wherein said optional substituent is selected from alkyl, alkoxy, OH, F, Cl, CN, COOR8, CONR8R9, $CF_3$; wherein R8 and R9 are independently selected from H and alkyl and alkyl and alkoxy are as defined according to formula (I) above.

Compounds of formula (I), formula (III) or formula (IV) wherein, B is selected from optionally substituted isoquinolinyl, wherein said optional substituent is $NH_2$; and 1H-pyrrolo[2,3-b]pyridine.

In an aspect, the invention comprises a compound selected from:

6-{[1-(2-Phenyl-thiazol-4-ylmethyl)-1H-pyrrolo[3,2-c]pyridin-4-ylamino]-methyl}-isoquinolin-1-ylamine;

6-[(1-Benzyl-1H-pyrrolo[3,2-c]pyridin-4-ylamino)-methyl]-isoquinolin-1-ylamine;

1-(4-{4-[(1H-Pyrrolo[2,3-b]pyridin-5-ylmethyl)-amino]-pyrrolo[3,2-c]pyridin-1-ylmethyl}-benzyl)-1H-pyridin-2-one;

[1-(2-Phenyl-thiazol-4-ylmethyl)-1H-pyrrolo[3,2-c]pyridin-4-yl]-(1H-pyrrolo[2,3-b]pyridin-5-ylmethyl)-amine;

(4-Aminomethyl-benzyl)-[1-(4-phenyl-butyl)-1H-pyrrolo[3,2-c]pyridin-4-yl]-amine;

(4-Aminomethyl-2-methyl-benzyl)-[1-(2-phenyl-thiazol-4-ylmethyl)-1H-pyrrolo[3,2-c]pyridin-4-yl]-amine;

1-{4-[4-(4-Aminomethyl-benzylamino)-pyrrolo[3,2-c]pyridin-1-ylmethyl]-benzyl}-1H-pyridin-2-one;

1-{4-[4-(4-Aminomethyl-2-methyl-benzylamino)-pyrrolo[3,2-c]pyridin-1-ylmethyl]-benzyl}-1H-pyridin-2-one;

(4-Aminomethyl-benzyl)-[1-(2-phenyl-thiazol-4-ylmethyl)-1H-pyrrolo[3,2-c]pyridin-4-yl]-amine;

(1-Amino-isoquinolin-6-ylmethyl)-{8-[4-(4-methyl-pyrazol-1-ylmethyl)-benzyl]-7,8-dihydro-6H-pyrimido[5,4-b][1,4]oxazin-4-yl}-amine;

and pharmaceutically acceptable salts and solvates thereof.

Therapeutic Applications

As previously mentioned, the compounds of the present invention are potent inhibitors of plasma kallikrein. They are therefore useful in the treatment of disease conditions for which over-activity of plasma kallikrein is a causative factor.

Accordingly, the present invention provides a compound of formula (I) for use in medicine.

The present invention also provides for the use of a compound of formula (I) in the manufacture of a medicament for the treatment or prevention of a disease or condition in which plasma kallikrein activity is implicated.

The present invention also provides a compound of formula (I) for use in the treatment or prevention of a disease or condition in which plasma kallikrein activity is implicated.

The present invention also provides a method of treatment of a disease or condition in which plasma kallikrein activity is implicated comprising administration to a subject in need thereof a therapeutically effective amount of a compound of formula (I).

In one aspect, diseases or conditions in which plasma kallikrein activity is implicated include impaired visual acuity, diabetic retinopathy, diabetic macular edema, hereditary angioedema, diabetes, pancreatitis, cerebral haemorrhage, nephropathy, cardiomyopathy, neuropathy, inflammatory bowel disease, arthritis, inflammation, septic shock, hypotension, cancer, adult respiratory distress syndrome, disseminated intravascular coagulation, cardiopulmonary bypass surgery and bleeding from post operative surgery.

In another aspect, the disease or condition in which plasma kallikrein activity is implicated is retinal vascular permeability associated with diabetic retinopathy and diabetic macular edema.

Combination Therapy

The compounds of the present invention may be administered in combination with other therapeutic agents. Suitable combination therapies include a compound of formula (I) combined with one or more agents selected from agents that inhibit platelet-derived growth factor (PDGF), endothelial growth factor (VEGF), integrin alpha5beta1, steroids, other agents that inhibit plasma kallikrein and other inhibitors of inflammation. Specific examples of therapeutic agents that may be combined with the compounds of the present invention include those disclosed in EP2281885A and by S. Patel in Retina, 2009 June; 29(6 Suppl):S45-8.

When combination therapy is employed, the compounds of the present invention and said combination agents may exist in the same or different pharmaceutical compositions, and may be administered separately, sequentially or simultaneously.

In another aspect, the compounds of the present invention may be administered in combination with laser treatment of the retina. The combination of laser therapy with intravitreal injection of an inhibitor of VEGF for the treatment of diabetic macular edema is known (Elman M, Aiello L, Beck R, et al. "Randomized trial evaluating ranibizumab plus prompt or deferred laser or triamcinolone plus prompt laser for diabetic macular edema". Ophthalmology. 27 Apr. 2010).

Definitions

The term "alkyl" includes saturated hydrocarbon residues including:

linear groups up to 10 carbon atoms ($C_1$-$C_{10}$), or of up to 6 carbon atoms ($C_1$-$C_6$), or of up to 4 carbon atoms ($C_1$-$C_4$). Examples of such alkyl groups include, but are not limited to, $C_1$-methyl, $C_2$-ethyl, $C_3$-propyl and $C_4$-n-butyl.

branched groups of between 3 and 10 carbon atoms ($C_3$-$C_{10}$), or of up to 7 carbon atoms ($C_3$-$C_7$), or of up to 4 carbon atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

each optionally substituted as stated above.

Cycloalkyl is a monocyclic saturated hydrocarbon of between 3 and 7 carbon atoms; wherein cycloalkyl may be optionally substituted with a substituent selected from alkyl, alkoxy and NR10R11; wherein R10 and R11 are independently selected from H and alkyl or R10 and R11 together with the nitrogen to which they are attached form a 4-, 5-, 6- or 7-membered heterocylic ring which may be saturated or unsaturated with 1 or 2 double bonds. Cycloalkyl groups may contain from 3 to 7 carbon atoms, or from 3 to 6 carbon atoms, or from 3 to 5 carbon atoms, or from 3 to 4 carbon atoms. Examples of suitable monocyclic cycloalkyl groups include cyclopropyl, cyclobutyl, cyclopentyl, cyclohexyl and cycloheptyl.

The term "alkoxy" includes O-linked hydrocarbon residues including:

linear groups of between 1 and 6 carbon atoms ($C_1$-$C_6$), or of between 1 and 4 carbon atoms ($C_1$-$C_4$). Examples of such alkoxy groups include, but are not limited to, $C_1$-methoxy, $C_2$-ethoxy, $C_3$-n-propoxy and $C_4$-n-butoxy.

branched groups of between 3 and 6 carbon atoms ($C_3$-$C_6$) or of between 3 and 4 carbon atoms ($C_3$-$C_4$). Examples of such alkoxy groups include, but are not limited to, $C_3$-iso-propoxy, and $C_4$-sec-butoxy and tert-butoxy.

each optionally substituted as stated above.

Unless otherwise stated, halo is selected from Cl, F, Br and I.

Aryl is as defined above. Typically, aryl will be optionally substituted with 1, 2 or 3 substituents. Optional substituents are selected from those stated above. Examples of suitable aryl groups include phenyl and naphthyl (each optionally substituted as stated above). Preferably aryl is selected from phenyl, substituted phenyl (substituted as stated above) and naphthyl.

Heteroaryl is as defined above. Examples of suitable heteroaryl groups include thienyl, furanyl, pyrrolyl, pyrazolyl, imidazoyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl, indolyl, benzimidazolyl, benzotriazolyl, quinolinyl and isoquinolinyl (optionally substituted as stated above). Preferably heteroaryl is selected from pyridyl, benzothiazole, indole, N-methylindole, thiazole, substituted thiazole, thiophenyl, furyl, pyrazine, pyrazole and substituted pyrazole; wherein substituents are as stated above.

The term "N-linked", such as in "N-linked heterocycloalkyl", means that the heterocycloalkyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

In groups such as —COOR*, "—" denotes the point of attachment of the substituent group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. For example (i) where a compound of the invention contains one or more acidic groups, for example carboxy groups, pharmaceutically acceptable base addition salts that can be formed include sodium, potassium, calcium, magnesium and ammonium salts, or salts with organic amines, such as, diethylamine, N-methyl-glucamine, diethanolamine or amino acids (e.g. lysine) and the like; (ii) where a compound of the invention contains a basic group, such as an amino group, pharmaceutically acceptable acid addition salts that can be formed include hydrochlorides, hydrobromides, sulfates, phosphates, acetates, citrates, lactates, tartrates, mesylates, succinates, oxalates, phosphates, esylates, tosylates, benzenesulfonates, naphthalenedisulphonates, maleates, adipates, fumarates, hippurates, camphorates, xinafoates, p-acetamidobenzoates, dihydroxybenzoates, hydroxynaphthoates, succinates, ascorbates, oleates, bisulfates and the like.

Hemisalts of acids and bases can also be formed, for example, hemisulfate and hemicalcium salts.

For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in 'The Practice of Medicinal Chemistry, $2^{nd}$ Ed. pp 561-585 (2003) and in F. J. Leinweber, *Drug Metab. Res.*, 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

In the context of the present invention, references herein to "treatment" include references to curative, palliative and prophylactic treatment.

General Methods

The compounds of formula (I) should be assessed for their biopharmaceutical properties, such as solubility and solution stability (across pH), permeability, etc., in order to select the most appropriate dosage form and route of administration for treatment of the proposed indication. They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Compounds of the invention intended for pharmaceutical use may be administered as a solid or liquid, such as a tablet, capsule or solution. Pharmaceutical compositions suitable for the delivery of compounds of the present invention and methods for their preparation will be readily apparent to those skilled in the art. Such compositions and methods for their preparation may be found, for example, in Remington's Pharmaceutical Sciences, 19th Edition (Mack Publishing Company, 1995).

Accordingly, the present invention provides a pharmaceutical composition comprising a compound of formula (I) and a pharmaceutically acceptable carrier, diluent or excipient.

For the treatment of conditions such as retinal vascular permeability associated with diabetic retinopathy and diabetic macular edema, the compounds of the invention may be administered in a form suitable for injection into the ocular region of a patient, in particular, in a form suitable for intravitreal injection. It is envisaged that formulations suitable for such use will take the form of sterile solutions of a compound of the invention in a suitable aqueous vehicle. The compositions may be administered to the patient under the supervision of the attending physician.

The compounds of the invention may also be administered directly into the blood stream, into subcutaneous tissue, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous or oily solutions. Where the solution is aqueous, excipients such as sugars (including but not restricted to glucose, manitol, sorbitol, etc.), salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

Parenteral formulations may include implants derived from degradable polymers such as polyesters (i.e., polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of co-solvents and/or solubility-enhancing agents such as surfactants, micelle structures and cyclodextrins.

In one embodiment, the compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

For administration to human patients, the total daily dose of the compounds of the invention is typically in the range 0.01 mg and 1000 mg, or between 0.1 mg and 250 mg, or between 1 mg and 50 mg depending, of course, on the mode of administration.

The total dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Synthetic Methods

The compounds of the present invention can be prepared according to the procedures of the following schemes and examples, using appropriate materials, and are further exemplified by the specific examples provided herein below. Moreover, by utilising the procedures described herein, one of ordinary skill in the art can readily prepare additional compounds that fall within the scope of the present invention claimed herein. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The compounds of the invention may be isolated in the form of their pharmaceutically acceptable salts, such as those described previously herein above.

It may be necessary to protect reactive functional groups (e.g. hydroxy, amino, thio or carboxy) in intermediates used in the preparation of compounds of the invention to avoid their unwanted participation in a reaction leading to the formation of the compounds. Conventional protecting groups, for example those described by T. W. Greene and P. G. M. Wuts in "Protective groups in organic chemistry" John Wiley and Sons, 4$^{th}$ Edition, 2006, may be used. For example, a common amino protecting group suitable for use herein is tert-butoxy carbonyl (Boc), which is readily removed by treatment with an acid such as trifluoroacetic acid or hydrogen chloride in an organic solvent such as dichloromethane. Alternatively the amino protecting group may be a benzyloxycarbonyl (Z) group which can be removed by hydrogenation with a palladium catalyst under a hydrogen atmosphere or 9-fluorenylmethyloxycarbonyl (Fmoc) group which can be removed by solutions of secondary organic amines such as diethylamine or piperidine in an organic solvents. Carboxyl groups are typically protected as esters such as methyl, ethyl, benzyl or tert-butyl which can all be removed by hydrolysis in the presence of bases such as lithium or sodium hydroxide. Benzyl protecting groups can also be removed by hydrogenation with a palladium catalyst under a hydrogen atmosphere whilst tert-butyl groups can also be removed by trifluoroacetic acid. Alternatively a trichloroethyl ester protecting group is removed with zinc in acetic acid. A common hydroxy protecting group suitable for use herein is a methyl ether, deprotection conditions comprise refluxing in 48% aqueous HBr for 1-24 hours, or by stirring with borane tribromide in dichloromethane for 1-24 hours. Alternatively where a hydroxy group is protected as a benzyl ether, deprotection conditions comprise hydrogenation with a palladium catalyst under a hydrogen atmosphere.

EXAMPLES

The invention is illustrated by the following non-limiting examples in which the following abbreviations and definitions are used:

| | |
|---|---|
| DCM | Dichloromethane |
| DMA | N,N-Dimethylacetamide |
| DMF | N,N-Dimethylformamide |
| EtOAc | Ethyl Acetate |
| HATU | 2-(3H-[1,2,3]triazolo[4,5-b]pyridin-3-yl)-1,1,3,3-tetramethylisouronium hexafluorophosphate(V) |
| hrs | Hours |
| HOBt | Hydroxybenzotriazole |
| LCMS | Liquid chromatography mass spectrometry |
| Me | Methyl |
| MeCN | Acetonitrile |
| MeOH | Methanol |
| Min | Minutes |
| MS | Mass spectrum |
| NMR | Nuclear magnetic resonance spectrum - NMR spectra were recorded at a frequency of 400 MHz unless otherwise indicated |
| Pet. Ether | Petroleum ether fraction boiling at 60-80° C. |
| Ph | Phenyl |
| rt | room temperature |
| THF | Tetrahydrofuran |
| TFA | Trifluoroacetic acid |

All reactions were carried out under an atmosphere of nitrogen unless specified otherwise.

$^1$H NMR spectra were recorded on a Bruker (400 MHz) spectrometer with reference to deuterium solvent and at rt.

Molecular ions were obtained using LCMS which was carried out using a Chromolith Speedrod RP-18e column, 50×4.6 mm, with a linear gradient 10% to 90% 0.1% $HCO_2H$/MeCN into 0.1% $HCO_2H/H_2O$ over 13 min, flow rate 1.5 mL/min, or using Agilent, X-Select, acidic, 5-95% MeCN/water over 4 min. Data was collected using a Thermofinnigan Surveyor MSQ mass spectrometer with electrospray ionisation in conjunction with a Thermofinnigan Surveyor LC system.

Chemical names were generated using the Autonom software provided as part of the ISIS draw package from MDL Information Systems, in the IUPAC form using Chemaxon software.

Where products were purified by flash chromatography, 'silica' refers to silica gel for chromatography, 0.035 to 0.070 mm (220 to 440 mesh) (e.g. Merck silica gel 60), and an applied pressure of nitrogen up to 10 p.s.i accelerated column elution. Reverse phase preparative HPLC purifications were carried out using a Waters 2525 binary gradient pumping system at flow rates of typically 20 mL/min using a Waters 2996 photodiode array detector.

All solvents and commercial reagents were used as received.

General methods for the preparation of the compounds in Tables below are described here:—

General Method for Alkylation of the Bicyclic Nitrogen

To sodium hydride (2 eq) in DMF at 0° C. was added the free based bicyclic amine (1 eq) and the reaction stirred for 20 mins then benzyl bromide (1.1 eq) added and reaction stirred at room temperature for between 2-16 h. The cooled reaction mixture was quenched with water and extracted with EtOAc (2×) the combined organics were washed with water and brine, dried (MgSO4) and concentrated and purified as necessary.

General Procedures for Chloro Displacement with Primary Amines

A: The aryl chloride (1 eq) and the amine (1-5 eq) in ethanol were heated at 130° C. for between 8-120 h. The reaction mixture was concentrated in vacuo and purified as necessary.

B: The aryl chloride (1 eq) and the amine (1-5 eq) in n-butanol were heated at 130° C. for between 8-120 h. The reaction mixture was concentrated in vacuo and purified as necessary.

C: To the aryl chloride (1 eq) in a microwave tube in dry toluene was added the amine (1-1.4 eq), BINAP (0.8 eq) and sodium tert-butoxide (1.4 eq). A flow of $N_2$ was passed through reaction mixture for 5 mins. Finally $Pd_2dba_3$ (0.3 eq) added and reaction stirred for 1 min before placing immediately in the microwave at 170° C. for between 30-90 mins. The reaction mixture was concentrated and purified either by flash chromatography or by reverse phase prep HPLC.

General Method for Nitrile Reduction

To the cooled nitrile (1 eq) in methanol was added nickel (II) chloride hexahydrate (0.1 eq) and di-tert-butyl dicarbonate (2 eq). The sodium borohydride (7 eq) was added portionwise to control the gas evolution. The reaction mixture was stirred at 0° C. to room temperature for 18 hours after which time the MeOH was removed by evaporation. The residue was dissolved in $CHCl_3$, washed with saturated $NaHCO_3$, water, brine, dried ($Na_2SO_4$) and filtered. The filtrate was evaporated and purified as necessary.

General Method for Boc Deprotection

To the Boc protected benzylamine was added 4M HCl in dioxane and the reaction stirred at room temperature for between 1-16 h. The solvent was removed in vacuo to afford the target as the HCl salt Example 7

1-{4-[4-(4-Aminomethyl-benzylamino)-pyrrolo[3,2-c]pyridin-1-ylmethyl]-benzyl}-1H-pyridin-2-one

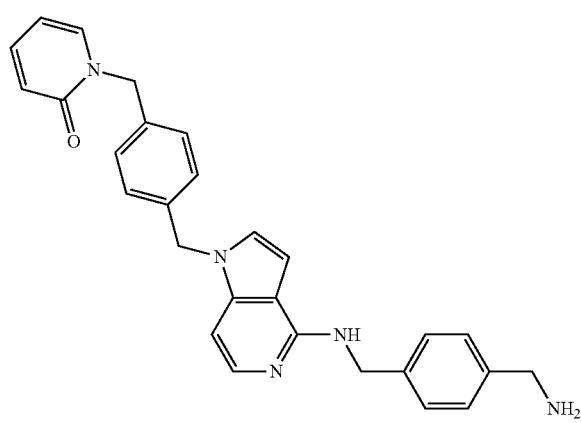 [SMILES: NCc1ccc(CNc2nccc3c2ccn3Cc2ccc(Cn3ccccc3=O)cc2)cc1]

A. 1-(4-Hydroxymethyl-benzyl)-1H-pyridin-2-one 4-(Chloromethyl)benzylalcohol (5 g, 31.93 mmol) was dissolved in acetone (150 ml), and 2-hydroxypyridine (3.6 g, 38.31 mmol) and potassium carbonate (13.2 g, 95.78 mmol) were added. The reaction mixture was stirred at 50° C. for 3 hours. The solvent was removed in vacuo and the residue taken up in chloroform (100 mL). The organic layer was washed with water (30 mL), brine (30 mL), dried (Na$_2$SO$_4$), filtered and evaporated. The residue was purified by flash chromatography eluting with 5% MeOH-DCM to give a white solid identified as the title compound (5.4 g, 25.09 mmol, 79% yield).

[M+Na]+=237.8

B. 1-(4-Bromomethyl-benzyl)-1H-pyridin-2-one 1-(4-Hydroxymethyl-benzyl)-1H-pyridin-2-one (1 g, 4.65 mmol) was dissolved in DCM (75 ml) and phosphorous tribromide (2.5 g, 9.29 mmol) was added. The reaction was stirred at room temperature for 3 hrs. On completion, the reaction mixture was diluted with CHCl$_3$ (75 mL) and washed with saturated NaHCO$_3$ (30 mL), water (30 mL) and brine (30 mL). The organic layer was dried (Na$_2$SO$_4$), filtered and evaporated to give a white solid identified as the title compound which was used without further purification (1.05 g, 3.78 mmol, 81% yield).

[M+H]$^+$=277.61 and 279.59

C. 4-[(1H-Pyrrolo[3,2-c]pyridin-4-ylamino)-methyl]-benzonitrile 4-(Aminomethyl)benzonitrile. HCl was partitioned between chloroform (50 mL) and saturated NaHCO$_3$ (10 mL), dried over Na$_2$SO$_4$, filtered and evaporated to afford 4-(aminomethyl)benzonitrile free base as a yellow oil. To 4-(aminomethyl)benzonitrile (250 mg, 1.89 mmol) was added 4-chloro-5-azaindole (289 mg, 1.89 mmol) in ethanol (1 mL) and the mixture was heated at 130° C. for 35 hours, adding minimum ethanol when evaporated. The crude residue was purified by flash chromatography eluting with 4% to 12% MeOH-DCM to give a pale yellow gum identified as the title compound (300 mg, 1.21 mmol, 64% yield).

[M+H]+=248.7

D. {4-[(1H-Pyrrolo[3,2-c]pyridin-4-ylamino)-methyl]-benzyl}-carbamic acid tert-butyl ester 4-[(1H-Pyrrolo[3,2-c]pyridin-4-ylamino)-methyl]-benzonitrile (300 mg, 1.21 mmol) was dissolved in MeOH (30 ml) and cooled to 0° C. Nickel (II) chloride hexahydrate (29 mg, 0.12 mmol) and di-tertbutyl dicarbonate (527 mg, 2.42 mmol) were added followed by sodium borohydride portionwise (320 mg, 8.46 mmol) over 10 min. The reaction mixture was stirred at 0° C. to rt for 4 hours after which time the MeOH was removed by evaporation. The residue was dissolved in CHCl$_3$ (100 ml), washed with saturated NaHCO$_3$ (30 ml), water (30 ml), brine (30 ml), dried (Na$_2$SO$_4$), filtered and evaporated. The crude residue was purified by flash chromatography eluting with 12% MeOH-DCM to give an off white solid identified as the title compound (180 mg, 0.51 mmol, 42% yield).

[M+H]+=352.8

E. [4-({1-[4-(2-Oxo-2H-pyridin-1-ylmethyl)-benzyl]-1H-pyrrolo[3,2-c]pyridin-4-ylamino}-methyl)-benzyl]-carbamic acid tert-butyl ester {4-[(1H-Pyrrolo[3,2-c]pyridin-4-ylamino)-methyl]-benzyl}-carbamic acid tert-butyl ester (70 mg, 0.20 mmol) was dissolved in dry DMF (7 mL), placed under nitrogen and cooled to 0° C. NaH (60% in mineral oil, 16 mg, 0.40 mmol) was added, reaction allowed to warm to rt and stirred for 15 min at rt. During this time the solution turned from a pale yellow colour to a deep red/orange. The reaction mixture was then cooled to 0° C. and 1-(4-bromomethyl-benzyl)-1H-pyridin-2-one (66 mg, 0.24 mmol) in DMF (3 mL) added dropwise, then allowed to warm to rt and stirred for 3 hours at rt. The reaction mixture was quenched with water and diluted with ethyl acetate (50 mL). The organic layer was washed with saturated NaHCO$_3$ (20 mL), water (3×20 mL), brine (20 mL), dried (Na$_2$SO$_4$), and evaporated under vacuum. The crude material was purified by flash chromatography eluting with 8% MeOH-DCM to give a pale yellow gum identified as the title compound (40 mg, 0.073 mmol, 37% yield).

[M+H]+=550.0

F. 1-{4-[4-(4-Aminomethyl-benzylamino)-pyrrolo[3,2-c]pyridin-1-ylmethyl]-benzyl}-1H-pyridin-2-one

[4-({1-[4-(2-Oxo-2H-pyridin-1-ylmethyl)-benzyl]-1H-pyrrolo[3,2-c]pyridin-4-ylamino}-methyl)-benzyl]-carbamic acid tert-butyl ester (40 mg, 0.07 mmol) was dissolved in MeOH (1 ml) and treated with 4N HCl in dioxan (4 ml). After three hours at rt the solvent was removed in vacuo and the residue azeotroped with toluene (10 ml). The crude reaction mixture was purified by preparative HPLC to afford an off white solid identified as the title compound as a bis trifluoroacetic acid salt (24 mg, 0.035 mmol, 49% yield).

[M+H]+=449.8

NMR (d6-DMSO) δ 4.03 (2H, d, J=5.8 Hz), 4.76 (2H, d, J=6.2 Hz), 5.05 (2H, s), 5.48 (2H, s), 6.21-6.24 (1H, m), 6.38 (1H, d, J=8.9 Hz), 7.12 (1H, d, J=3.2 Hz), 7.21-7.28 (5H, m), 7.39-7.46 (5H, m), 7.53 (1H, t, J=6.2 Hz), 7.64 (1H, d, J=3.3 Hz), 7.77 (1H, dd, J=6.6, 1.7 Hz), 8.17 (3H, s), 9.39 (1H, d, J=5.8 Hz), 12.63 (1H, d, J=5.0 Hz) ppm.

Example 10

(1-Amino-isoquinolin-6-ylmethyl)-{8-[4-(4-methyl-pyrazol-1-ylmethyl)-benzyl]-7,8-dihydro-6H-pyrimido[5,4-b][1,4]oxazin-4-yl}-amine

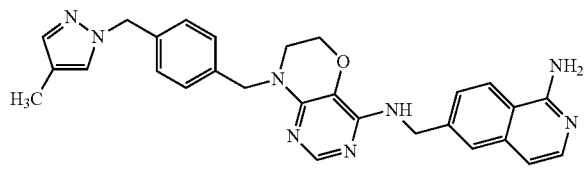 [SMILES: Cc1cnn(Cc2ccc(CN3CCOc4c(NCc5ccc6c(N)nccc6c5)ncnc43)cc2)c1]

A. 2-((E)-2-Dimethylamino-vinyl)-terephthalonitrile ester

Methylterephthalonitrile (1.42 g, 9.99 mmol) and Bredereck's reagent (3.48 g, 19.98 mmol) were dissolved in DMF (15 mL). The reaction mixture was heated at 75° C. under nitrogen for 72 hrs after which time the solvent was removed in vacuo. Trituration with Pet Ether gave a bright yellow solid identified as 2-((E)-2-dimethylamino-vinyl)-terephthalonitrile ester (1.88 g, 0.95 mmol, 95%).

¹H NMR (CD₃OD) δ: 3.20 (6H, s), 5.34 (1H, d, J=13.4 Hz), 7.21 (1H, dd, J=8.0 Hz, 1.4 Hz), 7.9 (1H, d, 13.4 Hz), 7.61 (1H, d, J=8.0 Hz), 7.94 (1H, d, J=1.2 Hz)

B. 1-Amino-2-(2,4-dimethoxy-benzyl)-1,2-dihydro-isoquinoline-6-carbonitrile 2-((E)-2-Dimethylamino-vinyl)-terephthalonitrile ester (1.85 g, 9.38 mmol) was dissolved in 1,3-dimethyl-3,4,5,6-tetrahydro-2(1H)-pyrimidinone (5 mL) and 2,4-dimethoxy-benzylamine (2.35 g, 14.07 mmol) was added. The reaction mixture was heated at 75° C. under nitrogen. After 3 hrs the reaction mixture was cooled and diethyl ether/Pet Ether (15:85) was added. The yellow solid was filtered off, dried in vacuo, and identified as 1-amino-2-(2,4-dimethoxy-benzyl)-1,2-dihydro-isoquinoline-6-carbonitrile (2.65 g, 8.38 mmol, 89%).

[M+H]⁺=320.0
¹H NMR (CD₃OD) δ: 3.85 (3H, s), 3.92 (3H, s), 5.02 (2H, s), 6.39 (1H, d, J=7.4 Hz), 6.57 (1H, dd, J=8.4 Hz, 2.4 Hz), 6.66 (1H, d, 2.4 Hz), 7.18 (1H, d, 8.4 Hz), 7.24 (1H, d, 7.4 Hz), 7.72 (1H, dd, J=8.5 Hz, 1.4 Hz), 7.93 (1H, s), 8.45 (1H, d, J=8.5 Hz)

C. 1-Amino-isoquinoline-6-carbonitrile

1-Amino-2-(2,4-dimethoxy-benzyl)-1,2-dihydro-isoquinoline-6-carbonitrile (1.6 g, 5.0 mmol) was dissolved in anisole (17 mL) and trifluoroacetic acid (20 mL). The reaction mixture was heated at 105° C. under nitrogen for 12 hrs after which time the reaction mixture was cooled, diethyl ether/Pet Ether (3:7) was added, the resultant solid was filtered off, dried in vacuo and identified as 1-amino-isoquinoline-6-carbonitrile (770 mg, 4.54 mmol, 91%).

[M+H]⁺=170.0
¹H NMR (CD₃OD) δ: 7.23-7.25 (1H, d, J=6.9 Hz), 7.65 (1H, d, J=6.8 Hz), 8.11 (1H, dd, J=8.7 Hz, 1.6 Hz), 8.33 (1H, s), 8.45 (1H, d, J=8.7 Hz).

D. (1-Amino-isoquinolin-6-ylmethyl)-carbamic acid tert-butyl ester

1-Amino-isoquinoline-6-carbonitrile (200 mg, 1.18 mmol) was dissolved in methanol (20 mL). This solution was cooled to 0° C. Nickel (II) chloride hexahydrate (28 mg, 0.12 mmol) and di-tertbutyl dicarbonate (516 g, 2.36 mmol) were added followed by sodium borohydride (313 g, 8.22 mmol) portionwise. The reaction mixture was stirred at 0° C. to room temp for 3 days. The MeOH was removed by evaporation. The residue was dissolved in CHCl₃ (70 ml), washed with sat NaHCO₃ (1×30 mL), water (1×30 mL), brine (1×30 mL), dried (Na₂SO₄) and evaporated in vacuo to give a yellow oil identified as (1-amino-isoquinolin-6-ylmethyl)-carbamic acid tert-butyl ester (110 mg, 0.4 mmol, 34%).

[M+H]⁺=274.1.

E. 6-Aminomethyl-isoquinolin-1-ylamine Hydrochloride (1-Amino-isoquinolin-6-ylmethyl)-carbamic acid tert-butyl ester (110 mg, 0.40 mmol) was dissolved in 4M HCl in dioxan (40 mL). After 18 hrs at room temperature the solvent was removed in vacuo to give a pale brown solid identified as 6-aminomethyl-isoquinolin-1-ylamine hydrochloride (67 mg, 0.39 mmol, 96%).

[M+H]⁺=174.3

F. (4-((4-Methyl-1H-pyrazol-1-yl)methyl)phenyl)methanol

To a round bottom flask under N₂ was added: (4-(chloromethyl)phenyl)methanol (10.04 g, 60.9 mmol), 4-methyl-1H-pyrazole (5.05 ml, 60.9 mmol) and dry MeCN (100 mL). Next, potassium carbonate (9.26 g, 67.0 mmol) was added and the white suspension was heated to 60° C. for 18 h. The volatiles were removed in vacuo. The residue was partitioned between EtOAc (100 mL) and water (150 mL). Aqueous layer was neutralised to pH 7 with 1 N HCl and extracted with EtOAc (2×100 mL). The combined organic layers were washed with water (100 mL), brine (50 mL) then dried (MgSO₄), filtered and concentrated in vacuo. The crude product was purified by chromatography (10-80% EtOAc in iso-hexanes) to afford (4-((4-methyl-1H-pyrazol-1-yl)methyl)phenyl)methanol (2.9 g, 14.05 mmol, 23.07% yield) as a free-flowing oil that solidified on standing.

[M+H]⁺=203.2

G. 1-(4-(Bromomethyl)benzyl)-4-methyl-1H-pyrazole

To a flask under N₂ was added: (4-((4-methyl-1H-pyrazol-1-yl)methyl)phenyl)methanol (250 mg, 1.236 mmol), triphenylphosphine (373 mg, 1.421 mmol) and dry DCM (5.0 mL). Cooled in an ice bath before perbromomethane (451 mg, 1.360 mmol) was added. Stirred at rt for 1 h. Concentrated in vacuo and purified by column chromatography (0-20% EtOAc in iso-hexanes) to afford 1-(4-(bromomethyl)benzyl)-4-methyl-1H-pyrazole (0.33 g, 1.182 mmol, 96% yield) as an oil that solidified on standing to a white solid.

[M+H]⁺=265.1/267.1

H. 2-[(6-Chloro-5-methoxy-4-pyrimidinyl)amino]-ethanol

To a solution of 4,6-dichloro-5-methoxypyrimidine (1.00 g, 5.59 mmol) in dioxane (15 mL) was added 2-aminoethanol (348 mg, 5.70 mmol) and potassium carbonate (926 mg, 6.70 mmol). The reaction was refluxed at 125° C. On completion, the reaction mixture was cooled to room temperature, the resulting suspension was filtered and the filtrate concentrated in vacuo. Both the filtered solid and the solid obtained from concentration of the filtrate were identified as the title compound and combined to afford 1.2 g (5.89 mmol, quantitative yield) of the title compound.

[M+H]⁺=203.9

I. 4-Chloro-7,8-dihydro-6H-pyrimido[5,4-b][1,4]oxazine

2-[(6-Chloro-5-methoxy-4-pyrimidinyl)amino]-ethanol (1.2 g, 5.89 mmol) was dissolved in a solution of boron tribromide (1.0 M in DCM, 40 mL) and the resulting reaction was heated to reflux and stirred for 3 hrs. The reaction mixture was cooled to rt, treated with ice-water (30 ml) and extracted with EtOAc (3×50 ml). The organic layer was dried (MgSO₄), filtered and concentrated in vacuo to afford the title compound as the HBr salt (0.96 g, 3.81 mmol, 65% yield).

[M+H]⁺=172.0

J. 4-Chloro-8-[4-(4-methyl-pyrazol-1-ylmethyl)-benzyl]-7,8-dihydro-6H-pyrimido[5,4-b][1,4]oxazine 4-Chloro-7,8-dihydro-6H-pyrimido[5,4-b][1,4]oxazine (109 mg, 0.64 mmol) was dissolved in DMF (2 ml) to which was added diisopropylethylamine (332 μl, 1.91 mmol) followed by 1-(4-(bromomethyl)benzyl)-4-methyl-1H-pyrazole (168 mg, 0.64 mmol). The reaction was stirred at room temperature overnight. The reaction mixture was diluted with CHCl₃ (40 ml) and washed sequentially with water (5×40 ml) and brine (40 ml). The organic layer was dried (MgSO₄), filtered and concentrated to afford a yellow solid. The crude material was purified by flash chromatography (8% MeOH/DCM-10% MeOH/DCM/1% NH₄OH). Fractions containing the title compound were concentrated to afford the title compound as a pale yellow oil (119 mg, 0.33 mmol, 52.6% yield).

LCMS: 355.9 @ 6.29 mins $^1$H NMR: (CDCl₃) 2.10 (3H, s), 4.29 (2H, t, J=9.4 Hz), 4.64 (2H, br. s), 5.21 (2H, s), 5.25 (2H, s), 7.19 (2H, d, J=8.1 Hz), 7.26 (1H, br. s), 7.34-7.37 (2H, m), 7.69 (2H, d, J=7.9 Hz).

K. (1-Amino-isoquinolin-6-ylmethyl)-{8-[4-(4-methyl-pyrazol-1-ylmethyl)-benzyl]-7,8-dihydro-6H-pyrimido[5,4-b][1,4]oxazin-4-yl}-amine 4-Chloro-8-[4-(4-methyl-pyrazol-1-ylmethyl)-benzyl]-7,8-dihydro-6H-pyrimido[5,4-b][1,4]oxazine (100 mg, 0.28 mmol) and 6-(aminomethyl)isoquinolin-1-ylamine (48.7 mg, 0.28 mmol) were suspended in ethanol (0.5 ml) and heated under microwave irradiation (CEM focussed microwave, Power 300W, 120° C. for 90 mins). The reaction was filtered and the solid washed with ethanol. The filtrate was concentrated under reduced pressure. The crude material was purified by preparative HPLC 0. Fractions containing product were combined and freeze dried to afford an off-white solid identified as the title compound (19.5 mg, 0.027 mmol, 10% yield).

[M+H]⁺=493.0

HPLC: 99% purity

1H NMR d6-DMSO: 1.98 (3H, s), 3.84 (2H, t, J=8.9 Hz), 4.45 (2H, t, J=8.9 Hz), 4.76 (2H, d, J=5.9 Hz), 4.92 (2H, s), 5.24 (2H, s), 7.21-7.17 (3H, m), 7.25 (1H, s), 7.50 (1H, s), 7.52 (2H, d, J=2.3 Hz), 7.56 (1H, dd, J=8.7, 1.6 Hz), 7.66 (1H, d, J=6.8 Hz), 7.69 (1H, s), 8.36 (1H, s), 8.52-8.46 (2H, m), 8.98 (2H, s).

The compounds in the following tables were synthesised as described in the general methods above and as described in Examples 7 and 10 above.

TABLE 1

| Example no. | A | B | Free base MW | [M + H]⁺ |
|---|---|---|---|---|
| 1 | 2-phenyl-thiazole | 1-aminoisoquinolin-6-yl | 462.57 | 462.9 |
| 2 | phenyl | 1-aminoisoquinolin-6-yl | 379.46 | 380.0 |
| 3 | 1-benzyl-pyridin-2(1H)-one | 1H-pyrrolo[2,3-b]pyridin-5-yl | 460.53 | 461.0 |

TABLE 1-continued

| Example no. | A | B | Free base MW | [M + H]⁺ |
|---|---|---|---|---|
| 4 | 2-phenylthiazol-4-yl | 7-azaindol-5-yl | 436.53 | 436.8 |
| 5 | 3-phenylpropyl | 4-(aminomethyl)phenyl | 384.52 | 385.1 |
| 6 | 2-phenylthiazol-4-yl | 4-(aminomethyl)-2-methylphenyl | 439.58 | 440.0 |
| 7 | 1-benzyl-2-oxo-pyridinyl | 4-(aminomethyl)phenyl | 449.55 | 449.8 |
| 8 | 1-benzyl-2-oxo-pyridinyl | 4-(aminomethyl)-2-methylphenyl | 463.57 | 464.0 |
| 9 | 2-phenylthiazol-4-yl | 4-(aminomethyl)phenyl | 425.55 | 423.0 |

TABLE 3

| Example No | Name |
|---|---|
| 1 | 6-{[1-(2-Phenyl-thiazol-4-ylmethyl)-1H-pyrrolo[3,2-c]-pyridin-4-ylamino]-methyl}-isoquinolin-1-ylamine |
| 2 | 6-[(1-Benzyl-1H-pyrrolo[3,2-c]pyridin-4-ylamino)-methyl]-isoquinolin-1-ylamine |
| 3 | 1-(4-{4-[(1H-Pyrrolo[2,3-b]pyridin-5-ylmethyl)-amino]-pyrrolo[3,2-c]pyridin-1-ylmethyl}-benzyl)-1H-pyridin-2-one |
| 4 | [1-(2-Phenyl-thiazol-4-ylmethyl)-1H-pyrrolo[3,2-c]pyridin-4-yl]-(1H-pyrrolo[2,3-b]pyridin-5-ylmethyl)-amine |
| 5 | (4-Aminomethyl-benzyl)-[1-(4-phenyl-butyl)-1H-pyrrolo[3,2-c]-pyridin-4-yl]-amine |
| 6 | (4-Aminomethyl-2-methyl-benzyl)-[1-(2-phenyl-thiazol-4-ylmethyl)-1H-pyrrolo[3,2-c]pyridin-4-yl]-amine |
| 8 | 1-{4-[4-(4-Aminomethyl-2-methyl-benzylamino)-pyrrolo[3,2-c]pyridin-1-ylmethyl]-benzyl}-1H-pyridin-2-one |
| 9 | (4-Aminomethyl-benzyl)-[1-(2-phenyl-thiazol-4-ylmethyl)-1H-pyrrolo[3,2-c]pyridin-4-yl]-amine |

TABLE 4

NMR data of examples (d6-DMSO)

| Example No | Chemical Shift (ppm) |
|---|---|
| 1 | 4.75 (2H, d, J = 6.3 Hz), 5.48 (2H, s), 6.37 (1H, d, J = 6.3 Hz), 6.77 (1H, s), 6.91 (1H, s), 7.33 (1H, s), 7.41 (2H, d, J = 6.3 Hz), 7.47-7.52 (4H, m), 7.64 (1H, d, J = 4.4 Hz), 7.89-7.92 (3H, m), 8.26 (1H, d, J = 6.3 Hz), s), 11.52 (1H, s) |
| 2 | 4.98 (2H, d, J = 6.3 Hz), 5.53 (2H, s), 6.37 (1H, d, J = 6.3 Hz), 6.77 (1H, s), 6.91 (1H, s), 7.33 (1H, s), 7.41 (2H, d, J = 4.4 Hz), 7.47-7.52 (4H, m), 7.64 (1H, d, J = 4.4 Hz), 7.89-7.92 (3H, m), 8.26 (1H, d, J = 6.3 Hz), s), 11.52 (1H, s) |
| 3 | 4.74 (2H, d, J = 6.3 Hz), 5.04 (2H, s), 5.30 (2H, s), 6.19-6.22 (1H, m), 6.38 (2H, d, J = 6.3 Hz), 6.74 (2H, d, J = 6.77 Hz), 7.13 (2H, d, J = 6.8 Hz), 7.21 (2H, d, J = 6.8 Hz), 7.25-7.26 (1H, m), 7.33-7.42 (2H, m), 7.59 (1H, d, J = 4.4 Hz), 7.72-7.74 (1H, m), 7.91 (1H, d, J = 6.3 Hz), 8.15 (1H, s), 8.25 (1H, d, J = 6.3 Hz), 11.52 (1H, s) |
| 4 | 4.75 (2H, d, J = 6.3 Hz), 5.48 (2H, s), 6.37 (1H, d, J = 6.3 Hz), 6.77 (1H, s), 6.91 (1H, s), 7.33 (1H, s), 7.41 (2H, d, J = 6.3 Hz), 7.47-7.52 (4H, m), 7.64 (1H, d, J = 4.4 Hz), 7.89-7.92 (3H, m), 8.26 (1H, d, J = 6.3 Hz), s), 11.52 (1H, s) |
| 5 | 1.50 (2H, quintet, J = 7.2 Hz), 1.72 (2H, quintet, J = 7.2 Hz), 1.85 (2H, br.s), 2.56 (2H, t, J = 8.0 Hz), 3.65 (2H, s), 4.08 (2H, t, J = 6.9 Hz), 4.63 (2H, d, J = 6.0 Hz), 6.65-6.68 (2H, m), 7.08 (1H, t, J = 6.2 Hz), 7.12-7.17 (4H, m), 7.21-7.27 (6H, m), 7.57 (1H, d, J = 5.9 Hz) |
| 6 | 4.50 (2H, d, J = 5.6 Hz), 5.05 (2H, s), 5.11 (2H, s), 6.21 (1H, dt, J = 1.4, 6.7 Hz), 6.37-6.41 (2H, m), 6.43 (1H, d, 9.5 Hz), 7.23-7.27 (4H, m), 7.40 (1H, dq, J = 2.1, 9.2 Hz), 7.44 (1H, t, J = 2.8 Hz), 7.74 (1H, dd, J = 1.6, 6.8 Hz), 7.87 (1H, d, J = 1.6 Hz), 7.90 (1H, dd, J = 2.6, 9.5 Hz), 8.19 (1H, d, J = 2.0 Hz), 8.44 (1H, d, J = 2.5 Hz), 8.76 (1H, t, J = 5.6 Hz), 11.58 (1H, s). |
| 8 | 2.51 (3H, s), 3.98 (2H, s), 4.74 (2H, s), 5.06 (2H, s), 5.49 (2H, s), 6.23 (1H, s), 6.39 (1H, s), 7.25-7.78 (13H, m), 8.27 (2H, s), 9.35 (1H, s), 12.74 (1H, s). |
| 9 | 4.01 (2H, q, J = 5.6 Hz), 4.77 (2H, d, J = 6.3 Hz), 5.65 (2H, s), 7.132 (1H, s), 7.43-7.51 (8H, m), 7.60 (1H, d, J = 4.4 Hz), 7.60-7.68 (2H, m), 7.87-7.90 (2H, m), 8.12 (2H, br.s + 1HCl salt), 9.38 (1H, s), 12.59 (1H, br.s) |

Biological Methods

The ability of the compounds of formula (I) to inhibit plasma kallikrein may be determined using the following biological assays:

Determination of the $IC_{50}$ for Plasma Kallikrein

Plasma kallikrein inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human plasma kallikrein (Protogen) was incubated at 37° C. with the fluorogenic substrate H-DPro-Phe-Arg-AFC and various concentrations of the test compound. Residual enzyme activity (initial rate of reaction) was determined by measuring the change in optical absorbance at 410 nm and the $IC_{50}$ value for the test compound was determined.

Data acquired from these assays are shown in Table 6 below:

TABLE 5

| Example No | $IC_{50}$ (human PKal) nM |
|---|---|
| 1 | 6540 |
| 2 | 28900 |
| 3 | 5460 |
| 4 | 5320 |
| 5 | 29000 |
| 6 | 8590 |
| 7 | 5370 |
| 8 | 6300 |
| 9 | 8100 |
| 10 | 20500 |

Selected compounds were further screened for inhibitory activity against the related enzyme KLK1. The ability of the compounds of formula (I) to inhibit KLK1 may be determined using the following biological assay:

Determination of the $IC_{50}$ for KLK1

KLK1 inhibitory activity in vitro was determined using standard published methods (see e.g. Johansen et al., Int. J. Tiss. Reac. 1986, 8, 185; Shori et al., Biochem. Pharmacol., 1992, 43, 1209; Stürzebecher et al., Biol. Chem. Hoppe-Seyler, 1992, 373, 1025). Human KLK1 (Callbiochem) was incubated at 37° C. with the fluorogenic substrate H-DVal-Leu-Arg-AFC and various concentrations of the test compound. Residual enzyme activity (initial rate of reaction) was determined by measuring the change in optical absorbance at 410 nm and the $IC_{50}$ value for the test compound was determined.

Data acquired from this assay are shown in Table 7 below:

TABLE 7

(KLK1 Activity)

| Example No | IC$_{50}$ (human KLK1) nM |
|---|---|
| 1 | 5340 |
| 2 | 3740 |
| 3 | 5690 |
| 4 | 10300 |
| 5 | 38600 |
| 6 | 8140 |
| 7 | 29900 |
| 8 | 5300 |
| 9 | 8260 |
| 10 | 5040 |

The invention claimed is:

1. A compound as defined by formula (III) or formula (IV):

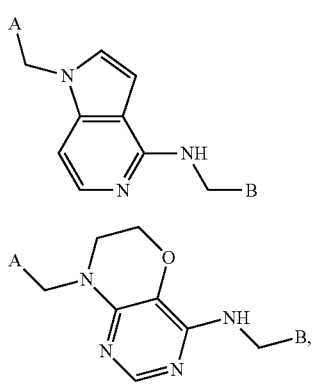

Formula (III)

Formula (IV)

wherein:
B is (i) or (ii):
i) a radical of formula II:

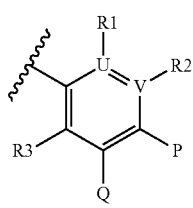

(II)

or
ii) a fused 6,5- or 6,6-heteroaromatic bicyclic ring, containing N and, optionally, one or two additional N, O, or S heteroatoms, which is optionally mono-, di or tri-substituted with a substituent that is alkyl, alkoxy, OH, halo, CN, COOR8, CONR8R9, CF$_3$ or NR8R9;
P is H and Q is —C(R20)(R21)NH$_2$, or P is —C(R20)(R21)NH$_2$ and Q is H;
U and V are independently C or N such that the aromatic ring containing U and V is phenyl, pyridine or pyrazine;
R1 is absent when U is N;
R2 is absent when V is N;

or, when present, R1 and R2 are independently H, alkyl, alkoxy, CN, halo or CF$_3$;
R3 is H, alkyl, alkoxy, CN, halo or CF$_3$;
A is —(CH$_2$)$_{0-9}$-heteroaryl or —(CH$_2$)$_{0-9}$-aryl;
R8 and R9 are independently H or alkyl;
R20 and R21 are independently H and alkyl, or may together form a cycloalkyl ring or a cyclic ether;
alkyl is a linear saturated hydrocarbon having up to 10 carbon atoms (C$_1$-C$_{10}$) or a branched saturated hydrocarbon of between 3 and 10 carbon atoms (C$_3$-C$_{10}$); alkyl may optionally be independently substituted with 1 or 2 substituents which are (C$_1$-C$_6$)alkoxy, OH, CN, CF$_3$, COOR10, CONR10R11, fluoro or NR10R11;
cycloalkyl is a monocyclic saturated hydrocarbon of between 3 and 7 carbon atoms;
a cyclic ether is a monocyclic saturated hydrocarbon of between 4 and 7 carbon atoms, wherein one of the ring carbons is replaced by an oxygen atom;
alkoxy is a linear O-linked hydrocarbon of between 1 and 6 carbon atoms (C$_1$-C$_6$) or a branched O-linked hydrocarbon of between 3 and 6 carbon atoms (C$_3$-C$_6$); alkoxy may optionally be independently substituted with 1 or 2 substituents which are OH, CN, CF$_3$, COOR10, CONR10R11, fluoro or NR10R11;
aryl is phenyl, biphenyl or naphthyl; aryl may be optionally independently substituted with 1, 2 or 3 substituents which are alkyl, alkoxy, methylenedioxy, ethylenedioxy, OH, halo, CN, morpholinyl, piperidinyl, heteroaryl, —(CH$_2$)$_{0-3}$—O-heteroaryl, aryl$^b$, —O-aryl$^b$, —(CH$_2$)$_{1-3}$-aryl$^b$, —(CH$_2$)$_{1-3}$-heteroaryl, —COOR10, —CONR10R11, —(CH$_2$)$_{1-3}$—NR14R15, CF$_3$ or —NR10R11;
aryl$^b$ is phenyl, biphenyl or naphthyl, which may be optionally independently substituted with 1, 2 or 3 substituents which are alkyl, alkoxy, OH, halo, CN, morpholinyl, piperidinyl, —COOR10, —CONR10R11, CF$_3$ or NR10R11;
heteroaryl is a 5, 6, 9 or 10 membered mono- or bi-cyclic aromatic ring, containing, where possible, 1, 2 or 3 ring members which are independently N, NR8, S or O; heteroaryl may be optionally independently substituted with 1, 2 or 3 substituents which are alkyl, alkoxy, OH, halo, CN, aryl, morpholinyl, piperidinyl, —(CH$_2$)$_{1-3}$-aryl, heteroaryl$^b$, —COOR10, —CONR10R11, CF$_3$ or —NR10R11;
heteroaryl$^b$ is a 5, 6, 9 or 10 membered mono- or bi-cyclic aromatic ring, containing, where possible, 1, 2 or 3 ring members which are independently N, NR8, S or O; wherein heteroaryl$^b$ may be optionally independently substituted with 1, 2 or 3 substituents which are alkyl, alkoxy, OH, halo, CN, morpholinyl, piperidinyl, aryl, —(CH$_2$)$_{1-3}$-aryl, —COOR10, —CONR10R11, CF$_3$ or NR10R11;
R10 and R11 are independently H or alkyl; or R10 and R11 together with the nitrogen to which they are attached form a 4-, 5-, 6- or 7-membered heterocyclic ring which may be saturated or unsaturated with 1 or 2 double bonds;
R14 and R15 are independently alkyl, aryl$^b$ or heteroaryl$^b$; or R14 and R15 together with the nitrogen to which they are attached form a 4-, 5-, 6- or 7-membered heterocyclic ring which may be saturated or unsaturated with 1 or 2 double bonds, and optionally may be oxo substituted;
or a tautomer, isomer, stereoisomer, or pharmaceutically acceptable salt or solvate thereof.

2. A compound according to claim 1, wherein B is (i) or (ii):
i) a radical of formula IIa:

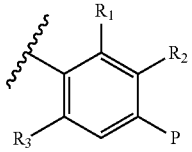

wherein R1 is H or alkyl, R2 is H, R3 is H or alkyl, and P is —CH₂NH₂; or
ii) a fused 6,5- or 6,6-heteroaromatic bicyclic ring, containing N and, optionally, one or two additional heteroatoms which are independently N, O or S, which is optionally mono or di-substituted with a substituent that is alkyl, alkoxy, OH, halo, CN, CF₃ or NR8R9.

3. A compound according to claim 1, wherein B is a radical of formula IIa:

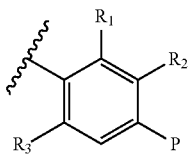

wherein R1 is H and alkyl, R2 is H, R3 is H or alkyl, and P is —CH₂NH₂.

4. A compound according claim 1, wherein B is (i) optionally substituted isoquinolinyl, wherein said optional substituent is NH₂, or (ii) 1H-pyrrolo[2,3-b]pyridine.

5. A compound according to claim 1, wherein A is heteroaryl substituted by phenyl; or —(CH₂)₀₋₃phenyl substituted by heteroaryl, or —(CH₂)₁₋₃-heteroaryl, or —(CH₂)₁₋₃—NR14R15.

6. A compound according to claim 1, wherein A is phenyl,

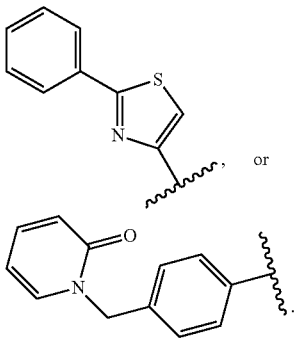

7. A compound according to claim 1, that is:
6-{[1-(2-Phenyl-thiazol-4-ylmethyl)-1H-pyrrolo[3,2-c]pyridin-4-ylamino]-methyl}-isoquinolin-1-ylamine;
6-[(1-Benzyl-1H-pyrrolo[3,2-c]pyridin-4-ylamino)-methyl]-isoquinolin-1-ylamine;
1-(4-{4-[(1H-Pyrrolo[2,3-b]pyridin-5-ylmethyl)-amino]-pyrrolo[3,2-c]pyridin-1-ylmethyl}-benzyl)-1H-pyridin-2-one;
[1-(2-Phenyl-thiazol-4-ylmethyl)-1H-pyrrolo[3,2-c]pyridin-4-yl]-(1H-pyrrolo[2,3-b]pyridin-5-ylmethyl)-amine;
(4-Aminomethyl-benzyl)-[1-(4-phenyl-butyl)-1H-pyrrolo[3,2-c]pyridin-4-yl]-amine;
(4-Aminomethyl-2-methyl-benzyl)-[1-(2-phenyl-thiazol-4-ylmethyl)-1H-pyrrolo[3,2-c]pyridin-4-yl]-amine;
1-{4-[4-(4-Aminomethyl-benzylamino)-pyrrolo[3,2-c]pyridin-1-ylmethyl]-benzyl}-1H-pyridin-2-one;
1-{4-[4-(4-Aminomethyl-2-methyl-benzylamino)-pyrrolo[3,2-c]pyridin-1-ylmethyl]-benzyl}-1H-pyridin-2-one;
(4-Aminomethyl-benzyl)-[1-(2-phenyl-thiazol-4-ylmethyl)-1H-pyrrolo[3,2-c]pyridin-4-yl]-amine;
(1-Amino-isoquinolin-6-ylmethyl)-{8-[4-(4-methyl-pyrazol-1-ylmethyl)-benzyl]-7,8-dihydro-6H-pyrimido[5,4-b][1,4]oxazin-4-yl}-amine;
or a pharmaceutically acceptable salt or solvate thereof.

8. A pharmaceutical composition comprising a compound as claimed in claim 1 and a pharmaceutically acceptable carrier, diluent or excipient.

9. The compound of claim 1, wherein the stereoisomer is an enantiomer, diastereoisomer, or racemic or scalemic mixture thereof.

10. The pharmaceutical composition of claim 8, wherein the compound is:
6-{[1-(2-Phenyl-thiazol-4-ylmethyl)-1H-pyrrolo[3,2-c]pyridin-4-ylamino]-methyl}-isoquinolin-1-ylamine;
6-[(1-Benzyl-1H-pyrrolo[3,2-c]pyridin-4-ylamino)-methyl]-isoquinolin-1-ylamine;
1-(4-{4-[(1H-Pyrrolo[2,3-b]pyridin-5-ylmethyl)-amino]-pyrrolo[3,2-c]pyridin-1-ylmethyl}-benzyl)-1H-pyridin-2-one;
[1-(2-Phenyl-thiazol-4-ylmethyl)-1H-pyrrolo[3,2-c]pyridin-4-yl]-(1H-pyrrolo[2,3-b]pyridin-5-ylmethyl)-amine;
(4-Aminomethyl-benzyl)-[1-(4-phenyl-butyl)-1H-pyrrolo[3,2-c]pyridin-4-yl]-amine;
(4-Aminomethyl-2-methyl-benzyl)-[1-(2-phenyl-thiazol-4-ylmethyl)-1H-pyrrolo[3,2-c]pyridin-4-yl]-amine;
1-{4-[4-(4-Aminomethyl-benzylamino)-pyrrolo[3,2-c]pyridin-1-ylmethyl]-benzyl}-1H-pyridin-2-one;
1-{4-[4-(4-Aminomethyl-2-methyl-benzylamino)-pyrrolo[3,2-c]pyridin-1-ylmethyl]-benzyl}-1H-pyridin-2-one;
(4-Aminomethyl-benzyl)-[1-(2-phenyl-thiazol-4-ylmethyl)-1H-pyrrolo[3,2-c]pyridin-4-yl]-amine;
(1-Amino-isoquinolin-6-ylmethyl)-{8-[4-(4-methyl-pyrazol-1-ylmethyl)-benzyl]-7,8-dihydro-6H-pyrimido[5,4-b][1,4]oxazin-4-yl}-amine;
or a pharmaceutically acceptable salt or solvate thereof.

11. A method of treatment of a disease or condition in which plasma kallikrein activity is implicated, the method comprising administering to a subject in need thereof a therapeutically effective amount of a compound as claimed in claim 1, wherein the disease or condition in which kallikrein activity is implicated is impaired visual acuity, diabetic retinopathy, diabetic macular edema, hereditary angioedema, diabetes, pancreatitis, cerebral haemorrhage, nephropathy, cardiomyopathy, inflammatory bowel disease, arthritis, septic shock, hypotension, adult respiratory distress syndrome, disseminated intravascular coagulation, blood coagulation during cardiopulmonary bypass surgery, bleeding from post-operative surgery, or retinal vascular permeability associated with diabetic retinopathy and diabetic macular edema.

12. The method of claim 11, wherein the disease or condition in which plasma kallikrein activity is implicated is retinal vascular permeability associated with diabetic retinopathy and diabetic macular edema.

13. The method of claim 11, wherein said compound is:
6-{[1-(2-Phenyl-thiazol-4-ylmethyl)-1H-pyrrolo[3,2-c]pyridin-4-ylamino]-methyl}-isoquinolin-1-ylamine;
6-[(1-Benzyl-1H-pyrrolo[3,2-c]pyridin-4-ylamino)-methyl]-isoquinolin-1-ylamine;
1-(4-{4-[(1H-Pyrrolo[2,3-b]pyridin-5-ylmethyl)-amino]-pyrrolo[3,2-c]pyridin-1-ylmethyl}-benzyl)-1H-pyridin-2-one;
[1-(2-Phenyl-thiazol-4-ylmethyl)-1H-pyrrolo[3,2-c]pyridin-4-yl]-(1H-pyrrolo[2,3-b]pyridin-5-ylmethyl)-amine;
(4-Aminomethyl-benzyl)-[1-(4-phenyl-butyl)-1H-pyrrolo[3,2-c]pyridin-4-yl]-amine;
(4-Aminomethyl-2-methyl-benzyl)-[1-(2-phenyl-thiazol-4-ylmethyl)-1H-pyrrolo[3,2-c]pyridin-4-yl]-amine;
1-{4-[4-(4-Aminomethyl-benzylamino)-pyrrolo[3,2-c]pyridin-1-ylmethyl]-benzyl}-1H-pyridin-2-one;
1-{4-[4-(4-Aminomethyl-2-methyl-benzylamino)-pyrrolo[3,2-c]pyridin-1-ylmethyl]-benzyl}-1H-pyridin-2-one;
(4-Aminomethyl-benzyl)-[1-(2-phenyl-thiazol-4-ylmethyl)-1H-pyrrolo[3,2-c]pyridin-4-yl]-amine;
(1-Amino-isoquinolin-6-ylmethyl)-{8-[4-(4-methyl-pyrazol-1-ylmethyl)-benzyl]-7,8-dihydro-6H-pyrimido[5,4-b][1,4]oxazin-4-yl}-amine;
or a pharmaceutically acceptable salt or solvate thereof.

14. The method of claim 11, wherein the disease or condition in which plasma kallikrein activity is implicated is cerebral haemorrhage in hyperglycemic patients.

15. The method of claim 11, wherein the disease or condition in which plasma kallikrein activity is implicated is impaired visual acuity.

16. The method of claim 11, wherein the disease or condition in which plasma kallikrein activity is implicated is hereditary angioedema.

17. The method of claim 11, wherein the disease or condition in which plasma kallikrein activity is implicated is diabetes.

18. The method of claim 11, wherein the disease or condition in which plasma kallikrein activity is implicated is cerebral haemorrhage.

19. The method of claim 11, wherein the disease or condition in which plasma kallikrein activity is implicated is nephropathy in diabetic patients.

20. The method of claim 11, wherein the disease or condition in which plasma kallikrein activity is implicated is cardiomyopathy.

21. The method of claim 11, wherein the disease or condition in which plasma kallikrein activity is implicated is inflammatory bowel disease or arthritis.

22. The method of claim 11, wherein the disease or condition in which plasma kallikrein activity is implicated is septic shock or hypotension.

23. The method of claim 11, wherein the disease or condition in which plasma kallikrein activity is implicated is adult respiratory distress syndrome.

24. The method of claim 11, wherein the disease or condition in which plasma kallikrein activity is implicated is disseminated intravascular coagulation.

25. The method of claim 11, wherein the disease or condition in which plasma kallikrein activity is implicated is blood coagulation during cardiopulmonary bypass surgery.

26. The method of claim 11, wherein the disease or condition in which plasma kallikrein activity is implicated is bleeding from post-operative surgery.

27. The method of claim 11, wherein the disease or condition in which plasma kallikrein activity is implicated is diabetic retinopathy.

28. The method of claim 11, wherein the disease or condition in which plasma kallikrein activity is implicated is diabetic macular edema.

29. A method of treating a disease or condition in which plasma kallikrein activity is implicated comprising administration to a subject in need thereof a therapeutically effective amount of a compound of claim 1, wherein the disease or condition in which plasma kallikrein activity is implicated is impaired visual acuity, diabetic retinopathy, diabetic macular edema, or hereditary angioedema.

* * * * *